United States Patent [19]
Still et al.

[11] Patent Number: 4,672,131
[45] Date of Patent: Jun. 9, 1987

[54] COMPOUNDS AND METHODS USEFUL FOR THE SYNTHESIS OF THROMBOXANE $A_2$

[75] Inventors: W. Clark Still; Philip R. Hamann; Shripad S. Bhagwat, all of New York, N.Y.

[73] Assignee: The Trustees of Columbia University in the City of New York, New York, N.Y.

[21] Appl. No.: 739,126

[22] Filed: May 30, 1985

[51] Int. Cl.[4] .................................. C07D 493/18
[52] U.S. Cl. .............................. 549/268; 549/363; 549/269
[58] Field of Search ........................... 549/268

[56] References Cited
PUBLICATIONS

Hamberg, M. et al., Proc. Nat'l. Acad. Sci. U.S.A., 72, (1975), pp. 2994–2998.
Ito, H. et al., Carbohydr. Res., 86, (1980), pp. 193–202.
Varma, A. J. et al., J. Org. Chem., 46, (1981), pp. 799–803.
Kong, F. et al., Carbohydr. Res., 112, (1983), pp. 141–147.
Fried, J. et al., J. Am. Chem. Soc. 106, (1984), pp. 3871–3872.
Granström, E. et al., *Prostaglandins and the Cardiovascular System*, John A. Oates, Ed., Raven Press, New York, (1982), pp. 15–58.

*Primary Examiner*—Norma S. Milestone
*Attorney, Agent, or Firm*—John P. White

[57] ABSTRACT

Compounds having the structure:

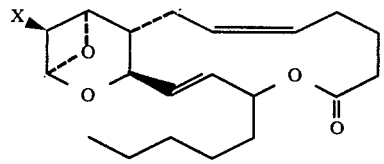

wherein X may be hydrogen, bromine, chlorine, fluorine or iodine are provided, together with methods for synthesizing these compounds, pharmaceutical compositions and use therof for reducing vascular blood flow.

Also provided are compounds having the structure:

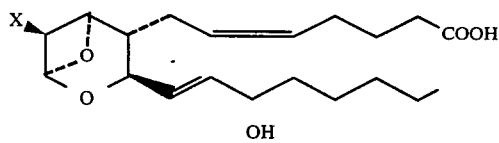

wherein X may be bromine, chlorine, fluorine or iodine, together with methods for preparing the compounds, pharmaceutical compositions and use thereof for reducing vascular blood flow.

2 Claims, 3 Drawing Figures

COMPOUNDS AND METHODS USEFUL FOR THE SYNTHESIS OF THROMBOXANE A₂

BACKGROUND OF THE INVENTION

The invention described herein was made in the course of work under Grant No. HL 25634 from the National Institutes of Health, U.S. Department of Health and Human Services. The U.S. Government has certain rights in this invention.

Throughout this application various publications are referenced by arabic numerals within parentheses. Full citations for these references may be found at the end of the specification immediately preceding the claims. The disclosures of these publications in their entireties are hereby incorporated by reference into this application in order to more fully describe the state of the art as known to those skilled therein as of the date of the invention described and claimed herein.

In 1975, Hamberg, Svensson and Samuelson (1) reported evidence for the existence of an unstable platelet-aggregating factor which they named thromboxane $A_2$ ($TXA_2$) and for which they proposed a novel bicyclic oxetane structure (A). A method for the preparation of the putative thromboxane $A_2$ ($TXA_2$) nucleus, an acid-labile 2,6-dioxa-[3.1.1]bicyloheptane, has been described (2). This method is now applied to the synthesis of $TXA_2$ itself. $TXA_2$ is an unstable substance $T_{\frac{1}{2}}(37°$ C.)=32 seconds in aqueous Krebs medium at pH 7.4) which is derived from the prostaglandin endoperoxide $PGH_2$ and which is an important blood platelet aggregation factor. (1,3) Although $TXA_2$ has not been previously isolated and characterized, its structure was proposed as A on the basis of its lability in neutral aqueous media, isotope incorporation experiments and the isolation of various $TXB_2$-like addition products. Structure is prepared by the method of the present invention.

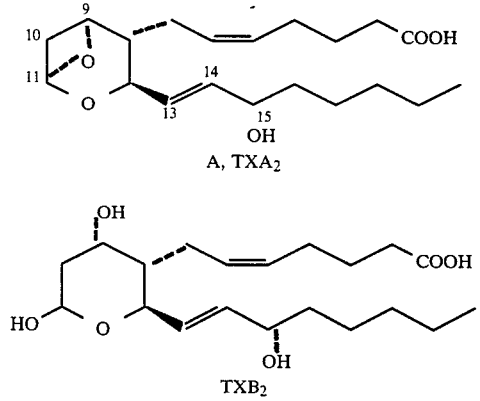

A, TXA₂

TXB₂

The synthetic material having structure is indistinguishable from platelet-derived $TXA_2$ in a variety of biological assays.

SUMMARY OF THE INVENTION

Compounds having the structure:

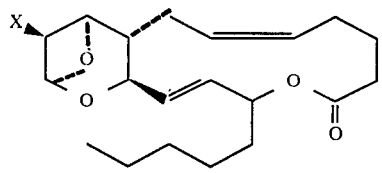

wherein X may be hydrogen, bromine, chlorine, fluorine or iodine are provided, together with methods for synthesizing these compounds, pharmaceutical compositions and use thereof for reducing vascular blood flow.

Also provided are compounds having the structure:

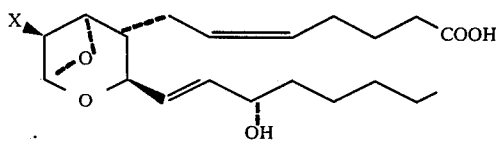

wherein X may be bromine, chlorine, fluorine or iodine, together with methods for preparing the compounds, pharmaceutical compositions and use thereof for reducing vascular blood flow.

DETAILED DESCRIPTION OF INVENTION

Figures 1A, 1B:
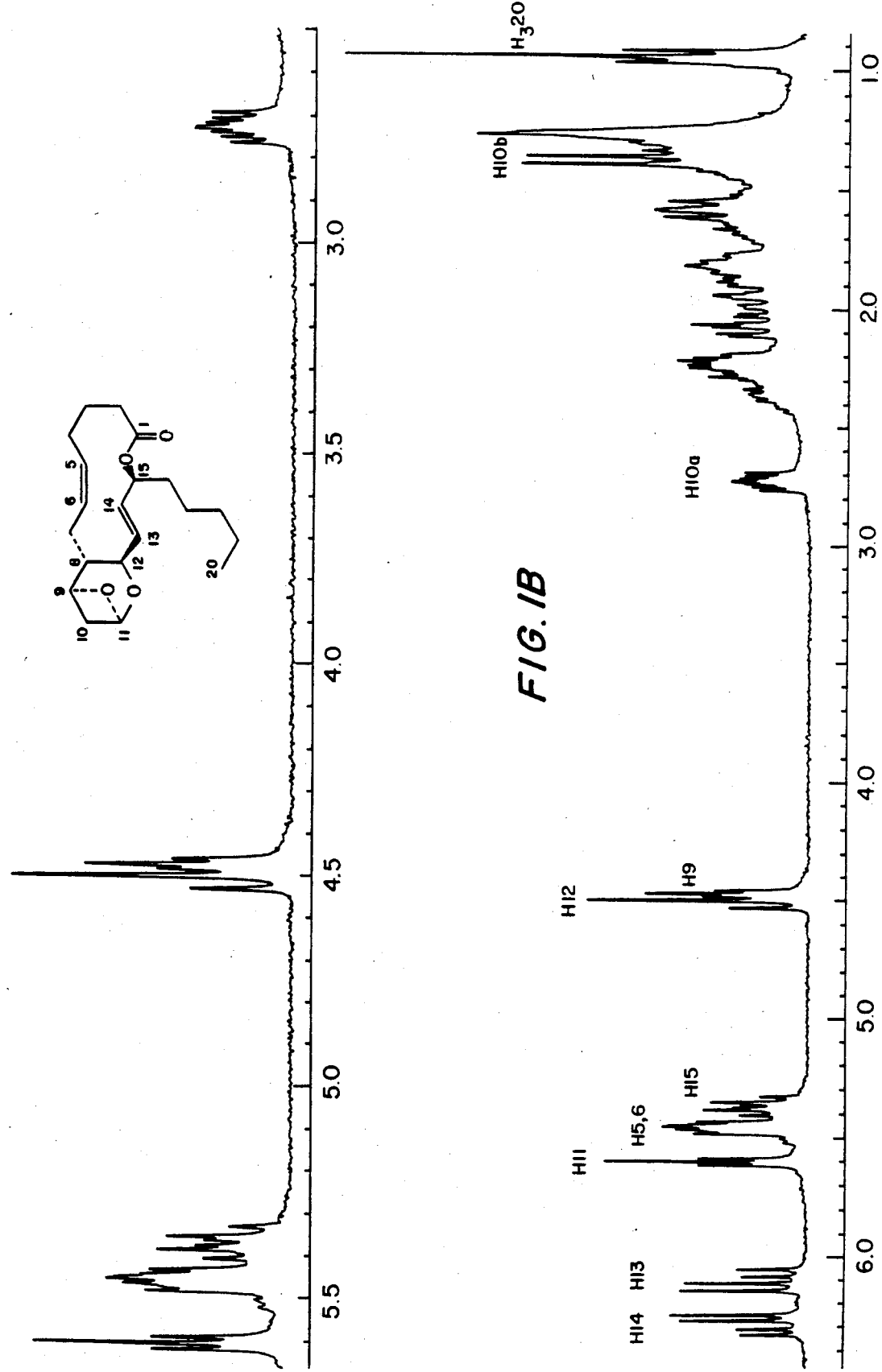
FIG. 1 is a 270 MHz ¹H NMR spectrum of synthetic 1,15-anhydro $TXA_2$ in benzene $D_6$. The lower trace shows the complete spectrum with assignments being confirmed by double resonance decoupling studies. The upper trace shows the expanded spectrum segment spanning 2.5–5.7 ppm.

The present invention provides compounds having the structure:

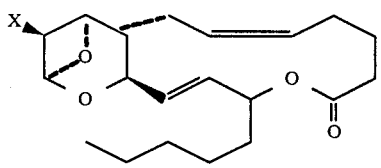

wherein X may be hydrogen, bromine, chlorine, fluorine or iodine. A preferred embodiment of the present invention is the above compound wherein X is bromine. These compounds may be used as intermediates in the synthesis of thromboxane $A_2$ ($TXA_2$). $TXA_2$ is a known platelet aggregating factor which may be used in diagnostic tests as a known standard to indicate deficiencies in $TXA_2$. $TXA_2$ is also known to constrict vascular smooth muscle tissue and may be useful in reducing vascular blood flow.

Pharmaceutical compositions which comprise one or more of the compounds of the present invention in an amount effective to reduce vascular blood flow and a pharmaceutically acceptable carrier may be prepared. Such suitable carriers are known to those skilled in the art. One generally used carrier is water, such as deionized distilled water. Other carriers include alcohols such as methyl alcohol or ethyl alcohol or aqueous mixtures thereof.

A method of reducing vascular blood flow in a subject, comprises administering to the subject an effective amount of the above compound.

The compounds of the present invention may also be used to produce halogen analogs of $TXA_2$ having the structure:

wherein X may be bromine, chlorine, fluorine or iodine. These halogen analogs also show activity in platelet aggregation as well as activity in constricting vascular smooth muscle tissue. A further embodiment of the present invention is a pharmaceutical composition which comprises an effective amount of a halogen analog of $TXA_2$ to reduce vascular blood flow and a pharmaceutically acceptable carrier.

Another method of reducing vascular blood flow in a subject comprises administering to the subject an effective amount of the above halogen analog of $TXA_2$.

Another aspect of the present invention is a method for preparing the compound of the present invention having the structure:

wherein X is bromine, chlorine, fluorine or iodine. This method comprises first treating thromboxane $B_2$ (Upjohn Company, Kalamazoo, Mich.) with a compound capable of inducing intramolecular esterification to form the compound having the structure:

A preferred compound for inducing intramolecul esterification is 2-thiopyridylchloroformate. Other compounds known to those skilled in the art to be capable of inducing intramolecular esterification to form a lactone structure may also be used.

Next, the product of the previous step is contacted with a compound capable of effecting a dehydration to form the beta-hydroxy enol ether. A preferred compound for effecting the dehydration is 2-chloro-1-methylpyridinium iodide. The beta-hydroxy enol ether is then contacted with a compound capable of effecting halohydrin formation to yield a compound having the structure:

wherein X may be bromine, chlorine, fluorine or iodine. Compounds suitable for effecting halohydrin formation are N-bromosuccinimide and N-chlorosuccinimide.

The intramolecular esterification step and the dehydration step both noted above, can be combined into a single step. In such a step the compound for inducing intramolecular esterification and the compound of effecting dehydration are the same compound, namely 2-chloro- 1-methylpyridinium iodide. The resulting product is the beta-hydroxy enol ether.

Finally, the product of the halohydrin formation step is reacted with a suitable ether-forming reagent under suitable conditions to form the compound of the present invention. The ether-forming reagent may be a mixture of an electrophilic reagent and a phosphorus containing reagent. A preferred embodiment utilizes the electrophilic reagent diethyl azodicarboxylate and the phosphorus containing reagent trimethyl phosphite. Other suitable electrophilic reagents are diisopropyl azodicarboxylate, di-tert-butyl azodicarboxylate, bis-N,N-dimethyazocarboxamide, and N-phenyl triazoline dione. Other suitable phosphorus containing reagents are phosphines, phosphonites, phosphonites, phosphinites, tributyl phosphite, triphenyl phosphite, triisopropoxy phosphite, triphenoxy phosphite, triethyl phosphite, diphenoxy-phenyl phosphite and trimethoxy phosphite.

Dehalogenation of the product of the previous step results in the formation of the compound of the present invention wherein X is hydrogen. The dehalogenation may be effected by tributyl tin hydride or polymer-bound tin hydride, as well as any other suitable reducing agent known to those skilled in the art.

The product of the dehalogenation step may be subjected to hydrolysis treatment resulting in the formation of the salt of $TXA_2$ The hydrolysis can be effected by any of the methods known to those skilled in the art. One method of hydrolysis utilizes a solution of sodium hydroxide, methanol and water. Another method of hydrolysis utilizes a solution of potassium trimethylsilyoxide and tetrahydrofuran.

The dehalogenation step can be omitted and the product resulting from the ether-forming step can be hydrolyzed directly. The resulting product would be a $TXA_2$ analog substituted at the 10-position with a halogen.

The free acid of $TXA_2$ may be formed by treating the salt of $TXA_2$, formed in the hydrolysis step, with any of the acids known to be suitable for such a purpose. One such acid is aqueous sodium dihydrogen phosphate.

EXPERIMENTAL DETAILS

The synthesis of $TXA_2$ began with $TXB_2$ (Upjohn Company, Kalamasoo, Mich.) which was esterified ($CH_2N_2$, $Et_2O$), peracetylated ($Ac_2O$, pyridine) and selectively deacetylated (cat. KOMe, MeOH, $-15°$ C.) at the more reactive C11 anomeric center to C in 78% overall yield. Dehydration to the unstable enol ether (MsCl, $Et_3N$, $CH_2Cl_2$), immediate bromohydrin formation (NBS, H$_2$O, THF) and deacetylation (K$_2$CO$_3$, MeOH, 25° C.) led to 10-bromo TXB$_2$ methyl ester (D) in 51% yield. Cyclization to the oxetane led to B (2) using a modified Mitsunobu reaction (4) ((MeO)$_3$P, EtO$_2$CN-NCO$_2$Et (DEAD), CH$_2$Cl$_2$, 25° C., 30 minutes) to provide E in 20% isolated yield. Although the yield was not high, E was well separated from the by-products by TLC and easily isolated in high purity by silica gel chromatography. In addition to approximately 25% starting material, other by-products of the cyclization included small amounts of enol ether products of simple and reductive elimination and a number of uncharacterized adducts with DEAD. Attempts to hydrolyze the DEAD adducts back to were unsuccessful. The product matched those of the model bicyclic bromooxetane system described previously (2) including the characteristic long range C9-C11 proton-proton coupling having J=3.9 Hz (see Examples).

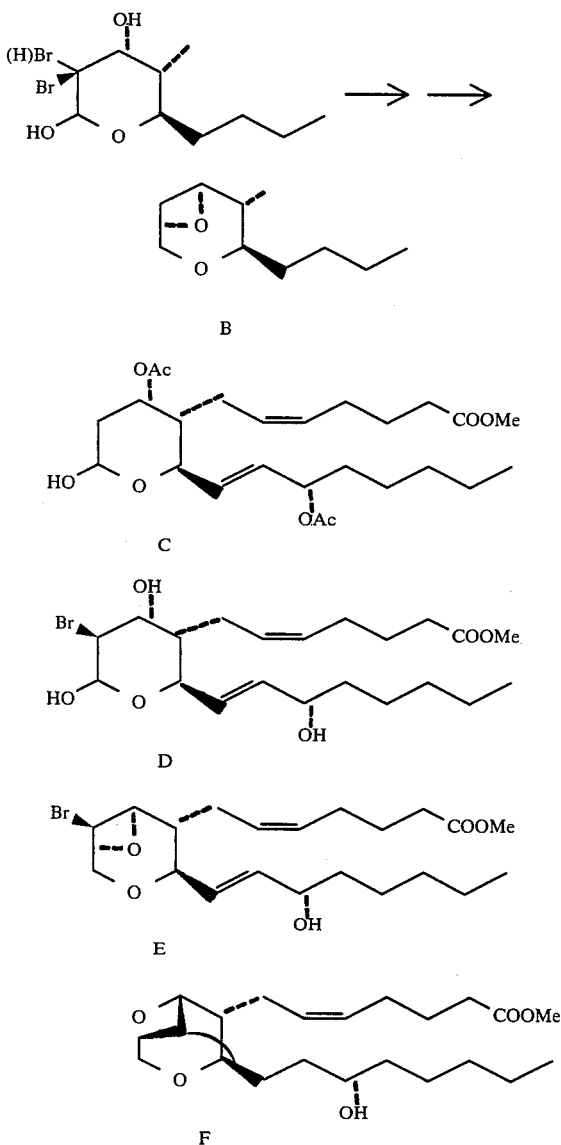

In contrast to the straightforward reductive behavior of the model which led from bromooxetane to B, however, free radical debromination (neat Bu$_3$SnH, Ph$_3$SnH or Bu$_2$SNH$_2$, sunlamp irradiation) of E did not lead to substantial quantities of the simple reduction product but instead to a material in which the C$_{13}$, C$_{14}$ olefin had been lost. The $^1$H NMR and MS of this undesired reduction product are compatible with the radical cyclization product F.

To prevent interaction of the intermediate C$_{10}$ free radical with the C$_{13}$, C$_{14}$ olefinic linkage, the olefin in principle could be protected, shifted to C14, C15 or somehow oriented away from C10. This last strategy is particularly appealing since it would require the least number of chemical transformations on the C12 sidechain and since any such chemistry would have to be compatible with the sensitive bicyclic oxetane nucleus after debromination. To conformationally restrict the approach of the intermediate C10 radical to the C13, C14 olefin, the C12 allylic alcohol sidechain was anchored to the C1 carboxyl by formation of the 1, 15-macrolactone. (5) Thus TXB$_2$ was converted to a 3.6:1 mixture of 1,15- and 1,9-macrolides via the thiopyridyl ester (6) (1. PyrSCOCL, Et$_3$N, Et$_2$O/CH$_2$Cl$_2$, 0° C.; 2. 2.5 mM in PhCH$_3$, 110° C., 15 hours) and the major 1,15-macrolide was isolated by silica gel chromatography in 65% yield. The minor 1,9-macrolide (18% yield) could be recycled with partial decomposition by saponification with LiOH/THF/H$_2$O back to TXB$_2$.

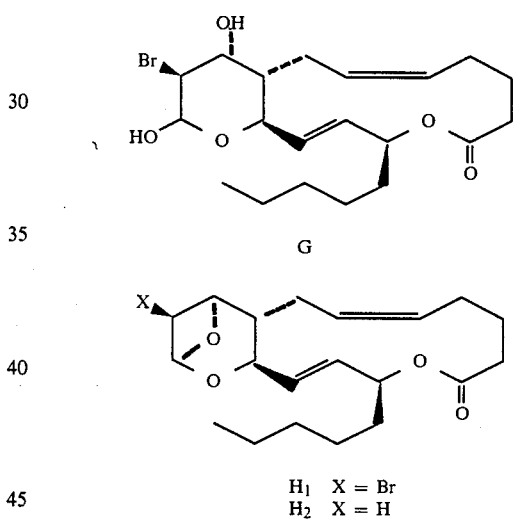

Dehydration at C11 was smoothly effected with the Mukaiyama reagent 2-chloro-1-methylpyridinium iodide (7) (Et$_3$N, CH$_3$CN, reflux) and immediate bromohydrin formation (NBS, Et$_2$O, H$_2$O) gave 10-bromo-1, 15-anhydro TXB$_2$ (G) in 65% yield. A simple alternative to the sequential macrolactonization and dehydration was direct treatment of TXB$_2$ with the Mukaiyama reagent to yield the same 10, 11-enol ether 1,15-macrolide intermediate prepared above but in lesser purity and in 30% yield. The dehydration of unprotected 2-deoxy pyranoses with the Mukaiyama reagent to unprotected glycals seems to be a unique transformation of some generality which could be of value in other synthetic endeavors.

Figure 2:
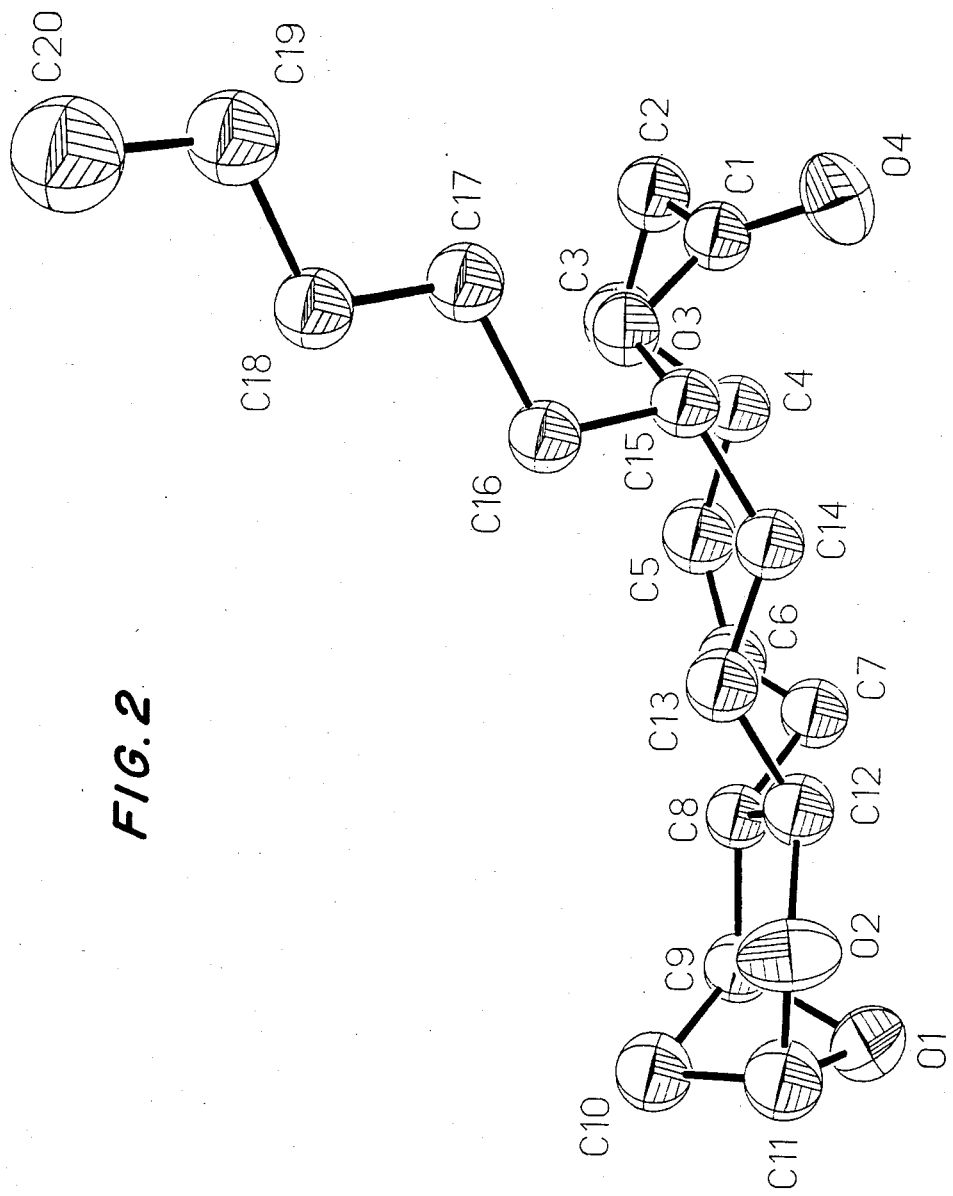
FIG. 2 is an X-ray crystal structure of the bicyclic oxetane structure of 1,5-anhydro $TXA_2$.

Modified Mitsunobu cyclization as in the methyl ester series provided the 10-bromo TXA$_2$ derivative H1 in 21% isolated yield at 81% conversion. A substantial effort was made to improve the yield of this key cyclization and variations in the solvent, the electrophilic component and the phosphorus component were investigated. Among solvents, yields were best in CH$_2$Cl$_2$ but Et$_2$O and CHCl$_3$ were almost as effective. The usual EtO$_2$ CN=NCO$_2$Et (DEAD) electrophile was more effective than the corresponding diisopropyl or di-tert.-butyl esters (10-15% yields) and the related bis-N, N-dimethyazocarboxamide and N-phenyltriazoline dione afforded only 5-10% of the desired bromooxetane. The cyclization reaction was quite sensitive to the structure of the phosphorus component and more than twenty phosphines, phosphites, phosphonites and phosphinites were evaluated. Relatively nucleophilic phosphines such as Bu$_3$P and Ph$_3$P gave substantial reductive elimination to the debrominated enol ether while more highly substituted phosphites (e.g. (iPrO)$_3$P, (PhO)$_3$P) reacted only sluggishly. Triethyl phosphite and (PhO)$_2$PPh proved comparable to trimethyl phosphite in the cyclization but showed no clear advantages. More classical base-promoted 1,3-eliminationss of intermediates having leaving a leaving group (e.g. trifluoroacetate, mesylate, triflate) at the anomeric C11 center provided only traces of the desired oxetane. With the optimal reagents, DEAD and (MeO)$_3$P in CH$_2$Cl$_2$, yields turned out to be best when large excesses of reagents were avoided and when the azo compound and the phosphite were premixed before addition to the cyclization precurson. Although a more effective cyclization would be quite valuable, the phosphite Mitsunobu cyclization is both simple and reproducible and the oxetane product (H1) is well resolved from the byproducts and is thus easily isolated by silica gel chromatography. With the C12 sidechain conformationally anchored by the 1,15-macrolactonic linkage, bromooxetane H1 cleanly yielded the desired 1,15-anhydro TXA$_2$ (H1) on reduction with tributyltin hydride. Compound H2 (X=H) displayed the characteristic bicyclic oxetane $^1$H and $^{13}$C NMR resonances which closely matched those of B. Its 270 MHz 1H NMR spectrum is shown in FIG. 1 and its novel bicyclic oxetane structure was confirmed by single crystal X-ray crystallography. No by-products in which the C13, C14 olefin had been lost could be found. Since H2 was unstable to chromatography and thus could not be entirely freed of Bu$_3$SnBR and excess Bu$_3$SnH, it was most readily prepared in high purity using a polymer-bound tin hydride (8) suspended in pentane (cat AIBN, 1-2 hours, 15° C., sunlamp irradiation) and could be isolated as a crystalline solid by filtration of the reagent and solvent evaporation (85% yield; mp(pentane)=81°-82° C.). The $^1$H and the $^{13}$C nmr resonances of the bicyclic oxetane nucleus correspond to those of E and the previously prepared model system B. The X-ray crystal structure (9) (FIG. 2) of H2 confirms both the structural assignment as the novel bicyclic oxetane structure of 1,15-anhydro TXA$_2$ and, at least in the crystal, the anticipated large spatial separation of C10 and C13.

A low resolution conformational analysis of compound H2 (C16-C20 replaced by a methyl) was conducted with molecular mechanics using the MM2 force field and starting from 104 macrocycle geometries generated at 60° dihedral angle resolution. This analysis showed the 13-membered macrolide to be quite flexible with more than a dozen different minimum energy conformations being found within 3 kcal/mole of the ground state. The majority of the conformers had C10 oriented close to the nodal plane of the C13, C14 olefin and thus could not easily lead to cyclization product observed in the methyl ester series described above. Two conformers (ca 1.0 and 2.5 kcal/mole above the ground state) did have C10 and the C13, C14 olefin approximately aligned for cyclization but with C10 and C13 rather widely separated (4.0 and 4.1A). The lowest energy conformation found was qualitatively the same as that found in the crystal.

When H2 is dissolved in 1:1 CD$_3$OD:D$_2$O containing 10 equiv. NaOD (30 minutes, 22° C. ), the macrolactone is saponified without loss of the bicyclic oxetane $^1$H NMR resonances to yield the sodium salt of A. H2 may also be opened in THF or Et$_2$O with Me$_3$O with Me$_3$SiOK (10) to yield the potassium salt of A ($^1$H NMR (THF-D$_8$) delta 5.87 (2H, br t, J 9 Hz, H13 & H14), 5.73 (1H, T, J 4 Hz, H11), 5.45-5.70 (2H, m, H5 & H6), 4.72 (1H, dd, J 4, 6 Hz, H9) 4.53 (1H, br t, J 6 Hz, H12), 4.18 (1H, br q, J 6 Hz, H15), 3.22 (1H, m, H10a)) which may be isolated with partial decomposition as an amorphous solid after solvent removal. Whereas H2 is biologically inactive, the methanol/water saponification solution shows marked activity which peaks 30 minutes after mixing and which reproduces the activities of natural platelet-derived TXA$_2$ in a variety of assays. In separately conducted experiments the sodium and potassium salts of synthetic A were found to be indistinguishable from natural TXA$_2$ as judged by their comparative potency in aggregating human platelets but not neutrophils, their constriction of vascular tissue including rabbit aorta, pulmonary, mesenteric and celiac arteries, their stability in plasma at 37° C. (half-life in Krebs medium at 37° C.=30 seconds leading to TXB$_2$) and their resistance to inhibition by selective thromboxane synthetase or cyclooxygenase inhibitors. (11)

While TXA$_2$ is rapidly hydrolyzed to TXB$_2$ in aqueous high salt, neutral pH buffers, its stability is appreciably enhanced at high pH. The salts of TXA$_2$ were stable for more than one week when stored at −20° C. either as isolated solids or in basic methanol or tetrahydrofuran solution. In aprotic solvents such as deuterochloroform, the free acid was generate by washing the sodium or potassium salt of A with aqueous sodium dihydrogen phosphate but it underwent elimination to the corresponding enol ether over the course of several hours.

These results give very strong support to the Samuelsson oxetane structure for TXA$_2$ as well as providing the first source of isolated TXA$_2$ for biological studies. The synthesis should also lend itself to the preparation of radiolabeled TXA$_2$ by substitution of tin tritiide for tin hydride in the final reduction step.

The present invention is further illustrated by reference to the examples which follow.

EXAMPLE 1

Thromboxane B$_2$ Methyl Ester 9,15-Diacetate (C)

To 190 mg (0.49 mmol) of thromboxane B$_2$ methyl ester (Upjohn Company, Kalamazoo, Mich.) in 1.4 ml of pyridine at 0° C. was added 0.7 ml (7.5 mmol, 15 eq) of acetic anhydride. The ice bath was allowed to melt and the reaction mixture was stirred at room temperature for 18 hours. The reaction mixture was diluted with 1:1 ether/petroleum ether and washed twice with 5% aqueous HCl, once with water, and once with saturated aqueous NaHCO$_3$. After drying over MgSO$_4$, the product was isolated by solvent evaporation and flash chromatography (silica gel, step gradient from 20% to 50% ethyl acetate in petroleum ether) to yield 225 mg (90%) of the desired triacetate and 12 mg (5%) of the 9,11-diacetate.

¹H NMR (CDCl₃) delta 5.93 (1H, dd, J=3, 10 Hz), 5.73 (1H, dd, J=6, 16 Hz), 5.60 (1H, dd, J=7, 16 Hz), 5.40 (1H, m), 5.3-5.15 (3H, m), 4.16 (1H, dd, J=8, 11 Hz), 3.65 (3H, S) 2.26 (2H, t, J=7 Hz), 2.10 (3H, s), 2.09 (3H, s) 2.02 (3H, s), 2.1-1.2 (17H, m), 0.86 (3H, br t, J=7 Hz).

¹³C NMR (CDCl₃) delta 173.58, 169.99, 169.74, 168.99, 133.10, 130.91, 129.18, 126.37, 90.46, 76.59, 73.22, 69.30, 51.25, 42.87, 34.55, 34.05, 33.14, 31.28, 26.31, 24.60, 24.43, 24.01, 22.25, 20.96, 20.95, 20.94, 13.90.

IR (CDCl₃) cm⁻¹ 1733, 1436, 1245, 1050.

MS (NH₃—CI) m/e 528 (M+NH₄), 468 (M—CH₂CO), 451 (M—CH₃CO₂).

TLC (silica gel, 25% ethyl acetate/pentane) R_f=0.16-0.21.

To 225 mg (0.44 mmol) of above triacetate in 5 ml of anhydrous MeOH at −15° C. was added 0.05 ml (0.08 mmol) of a 1.65M (saturated) solution of potassium tertbutoxide in tetrahydrofuran. The reaction mixture was allowed to warm to 0° C. over 30 minutes, diluted with 1:1 ether/petroleum and washed three times with water. After drying over MgSO₄, filtering, and concentrating, the crude product was chromatographed on silica gel (step gradient from 25% ethyl acetate in petroleum ether to neat ethyl acetate) to yield 180 mg (87%) of the 9,15-diacetate (C) as a mixture of anomers and 23 mg (ca 10%) of a mixture of other acetates.

¹H NMR (CDCl₃) (major anomer) delta 5.78 (1H, dd, J=6.5, 15.5 Hz), 5.63 (1H, dd, J=6.5, 15.5 Hz), 5.40 and 5.25 (2H, m), 5.25 (1H, m), 5.17 (1H, m), 5.02 (1H, m), 4 08 (1H, dd, J=8, 11 Hz), 3.64 (3H, s), 2.90 (1H, d, J=7 Hz), 2.30 (2H, br t, J=7 Hz), 2.08 (3H, s), 2.04 (3H, s), 2.2-1.2 (17H), 0.86 (3H, br t, J=7 Hz).

¹³C NMR (CDCl₃) (major anomer) delta 173.80, 170.17, 169.88, 132.78, 130.78, 130.07, 126.64, 92.21, 75.92, 73.46, 69.01, 51.38, 43.14, 37.21, 34.12, 33.25, 31.39, 26.39, 24.71, 24.51, 24.17, 22.36, 21.09. 20.99, 13.85.

IR (neat) cm⁻¹ 3420 (br), 1735, 1435, 1242, 1042, 1020, 920.

MS (CI, NH₃) m/e 486 (M+NH₄), 469 (M+1), 451 (M—OH).

HRMS Calcd for C₂₅H₃₉O₇ (M—OH) 451.2696. Found: 451.2650.

TLC (silca gel, 50% ethyl acetate/pentane) R_f=0.31-0.40.

EXAMPLE 2

10-Bromo Thromboxane B₂ Methyl Ester (D)

To 44 mg (0.094 mmol) of 9,15 diacetate (C) in 1 ml methylene chloride at 0° C. was added 0.13 ml (0.94 mmol, 10 eq) of triethylamine and 0.008 ml (0.1 mmol, 1.05 eq) methane sulfonyl chloride. The reaction was allowed to warm to room temperature for one hour before concentrating to about 0.1 ml. The concentrate was then transferred to the top of a chromatography column containing 1% triethylamine and eluted with 20% ethyl acetate in petroleum ether. After removing the solvent and pumping to dryness, the chromatographed product was taken up in 2 ml dry MeOH, cooled to 0° C. and treated with excess solid K₂CO₃. The reaction mixture was warmed to room temperature over a one hour period, diluted with 1:1 ether/petroleum and washed three times with water. After drying over MgSO₄, filtering and evaporating, ing, the crude acid-sensitive enol ether was obtained as a thick oil (20 mg, 58%). Pure material could be obtained by flash chromatography with 25% ethyl acetate in petroleum ether but the lability of the product made direct conversion to the bromohydrin below preferable.

¹H NMR (CDCl₁₃) delta 6.47 (1H, d, J=6 Hz), 5.88 (1H, dd, J=7, 16 Hz), 5.71 (1H, dd, J=8, 16 Hz), 5.46-5.39 (2H, m), 4.99 (1H, t, J=6 Hz), 4.21-4.11 (2H, m), 4.01 (1H, m), 3.65 (3H, s), 2.32 (2H, t, J=7 Hz), 2.2-1.2 (17H, m), 0.86 (3H, br t, J=7 Hz).

¹³C NMR (CDCl₃) delta 174.26, 146.04, 138.37, 130.59, 127.91, 127.78, 102.86, 75.59, 72.05, 60.19, 51.60, 43.68, 37.01, 33.01, 31.71, 26.58, 25.12, 27.21, 24.25, 22.58, 14.01.

IR (neat) cm⁻¹ 3447 (v br), 1740, 1643, 1232, 1021.

TLC (silca gel, 25% ethyl acetate/pentane) Rf =0.13.

To 3.4 mg (0.0093 mmol) of crude enol ether in 0.5 ml of tetrahydrofuran and 0.1 ml of water at 0° C. was added 1.7 mg (0.01 mmol) of powdered N-bromosuccinimide. After 10 minutes the reaction was diluted with ether, washed twice with saturated aqueous NaHCO₃, dried over MgSO₄, filtered, concentrated and flash chromatographed on silica gel (step gradient from 25% to 50% ethyl acetate in petroleum ether) to give 3.8 mg (88%) of an anomeric mixture of bromohydrines (D) as a thick oil.

¹H NMR (CDCl₃) delta 5.9-5.6 (2H, m), 5.45-5.25 (3H, m), 5.11 (0.5H, d, J=10 Hz), 5.02 (0.5H, dd, J=12, 2 Hz), 4.45-4.05 (5H), 3.65 (3H, s), 3.55 (0.5H, d, J=6 Hz), 3.40 (0.5H, d, J=12 Hz), 2.4-1.2 (17H), 0.68 (3H, br t, J=7 Hz).

¹³C NMR (CDCl₃) delta 175.16, 138.84, 138.74, 131.22, 130.99, 128.82, 128.43, 127.10, 127.39, 89.52, 94.80, 72.36, 76.64, 69.87, 72.27, 69.61, 69.22, 57.57, 47.75, 51.87, 38.25, 36.76, 33.22, 31.64, 26.48, 25.12, 24.70, 24.53, 23.98, 22.55, 13.96.

IR (CDCl₃) cm⁻¹ 3600, 3465 (br), 1720, 1438, 1229, 1155, 1097, 1046, 975.

MSD (CI-N3) 480 & 482 (M+NH₄), 462 and 464 (M+1), 445 and 447 (M+1-OH).

TLC (silica gel, 50% ethyl acetate/pentane) R_f=0.31-0.36.

10-Chloro Thromboxane B₂ Methyl Ester has been prepared using the same procedure except that N-chlorosuccinimide was substituted for N-bromosuccinimide. This 10-chloro compound can then be utilized in the same manner as the 10-bromo compound in the following examples.

EXAMPLE 3

10-Bromo Thromboxane A₂ Methyl Ester (E)

To a solution of 0.049 ml (0.41 mmol) distilled trimethyl phosphite in 1 ml dry methylene chloride (0° C., nitrogen) was added 0.049 ml (0.31 mmol) distilled diethyl azodicarboxylate (DEAD). The solution was stirred for 5 minutes at 25° C. and then a 0.10 ml aliquot (1.5 equiv (MeO)₃P, 1.1 equiv DEAD) was added to a well stirred 0° C. solution of 12 mg (0.026 mmol) 10-bromo thromboxane B₂ methyl ester (D) in 0.5 ml dry methylene chloride under nitrogen. The reaction mixture was stirred for 30 minutes at 25° C. and then most of the volatile material was removed under vacuum. The crude product was immediately flash chromatographed on slurry-packed silica gel with 20% tetrahydrofuran/2% triethylamine in petroleum ether. The bromooxetane product E was isolated as a colorless oil (2.5 mg, 20%).

¹H NMR (CDCl₃) delta 5.95 (1H, dd, J=15.7, 7.7 Hz), 5.83 (1H, dd, J=15.7, 5.6 Hz), 5.60 (dd, 1H, J=3.9, 3.3 Hz), 5.22-5.55 (2H, m), 4.92 (1H, dd, J=5.9, 3.3 Hz, 4.74 (1H, dd, J=5.9, 3.9 Hz), 4.21 (1H, m), 3.67 (3H, s), 2.31 (2H, m), 1.2-2.3 (15H), 0.87 (3H, t, J=6.7 Hz).

¹³C NMR (C₆D₆) delta 173.64, 138.16, 132.35, 128.18, 127.10, 106.13, 85.73, 77.41, 72.27, 51.47, 46.88, 42.17, 37.93, 33.66, 32.50, 27.82, 27.12, 25.88, 25.28, 23.39, 14.93.

IR (neat) cm⁻¹ 3312 (br), 2933, 2859, 1720, 1378, 1248, 1181, 1096, 848.

MS (CI—NH₃) m/e 462 and 464 (M+NH₄), 444 and 446 (M+NH₄—H₂O).

HRMS Calcd for C₂₁H₃₃ ⁷⁹BrO₅: 445.1589. Found: 445.1471.

TLC (silica gel, 20% tetrahydrofuran/pentane) R_f=0.27.

EXAMPLE 4

10-Bromo 1, 15-Anhydro Thromboxane B₂(G)

To 1.00 gm (2.70 mmol) of thromboxane B₂ (Upjohn Company, Kalamazoo, Mich. ) in 50 ml of ether was added 0.56 ml (4.05 mmol, 1.5 eq) of triethylamine (mixture was nonhomogeneous) and then 3.6 ml (2.97 mmol, 1.1 eq) of an 0.82M solution of 2-thiopyridylchloroformate (7) in methylene chloride. After 90 minutes of rapid stirring, the reaction mixture was transferred with ether directly to the top of a 2.7 cm×15 cm silica gel chomatography column which has be slurry-packed with 1% triethylamine in ethyl acetate. The column was eluted rapidly with a step-gradient of 0–10% acetone in ethyl acetate to yield the oily yellow thiopyridyl ester as a 4:1 mixture of anomers. Flushing the column with 30% methanol in ethyl acetate yielded 2–5% recovered thromboxane B₂.

¹H NMR (CDCl₃) delta (major anomer) 8.59 (1H, m), 7.72 (1H, dt, J=2, 8 Hz), 7.53 (1H, d, J=8 Hz), 7.29 (1H, dd, J=6, 8 Hz), 5.8-5.5 (2H, m), 5.4-5.2 (4H, m), 4.5-4.0 (4H, m), 2.70 (2H, m), 2.25-1.2 (18 H, m), 0.86 (3H, br t, J=7 Hz).

¹³C NMR (CDCl₃) delta (major anomer) 196.43, 150.84, 150.12, 138.13, 137.38, 130.28, 130.15, 129.34, 128.24, 123.63, 92.37, 72.14, 69.22, 64.68, 44.44, 43.05, 36.76, 36.21, 31.57, 25.80, 25.18, 25.02, 24.89, 22.46, 13.90.

IR (neat) cm⁻¹ 3380 (v br), 1710, 1570, 1450, 1420, 1100, 1020, 970.

MS (CI—NH₃) m/e 464 (M+1), 446 (M—OH), 428 (M—OH—H₂O).

TLC (silica gel, ethyl acetate) R_f=0.19-0.30.

The thiopyridyl ester was azeotropically dried by stripping twice with 50 ml of freshly distilled toluene under nitrogen at reduced pressure in a 1 liter flask. The flask was then fitted with a reflux condenser and a vacuum/argon line and evacuated to about 0.05 Torr for one hour. After venting with argon, 500 ml of toluene (freshly distilled from Na/Ph₂CO) was added to give a 5 mM solution and the reaction mixture was refluxed for 13 hours. The solvent was removed and the crude product was transferred to a separatory funnel with anhydrous ether. The material was then washed twice with 5% NaOH and once with brine, dried over MgSO₄ and stripped. Flash chromatography on a 2.7 cm×15 cm silica gel column with a step-gradient of 50% ethyl acetate in petroleum ether to pure ethyl acetate gave 618 mg (65%) of the crystalline 1,15-anhydro TXB₂ as a 5:1 mixture of anomers and 174 mg (18%) of impure 1, 9-anhydro TXB₂.

Major macrolide (1, 15-anhydro TXB₂):

¹H NMR (CDCl₃) delta (major or anomer) 6.08 (1H, dd, J=6, 16 Hz), 5.95 (1H, dd, J=7, 16 Hz), 5.57-5.13 (4H, m), 4.34 (1H, dd, J=7, 11 Hz), 4.1-4.0 (1H, m), 3.82 (1H, d, J=6 Hz), 2.43-2.32 (2H, m), 2.3-1.2 (18 H, m), 0.86 (3H, br t, J=7 Hz).

¹³C NMR (CDCl₃) delta (major anomer) 173.44, 133.88, 132.90, 129.08, 128.46, 92.63, 72.20, 67.04, 65.59, 48.43, 35.85, 34.20, 33.97, 31.41, 25.67, 25.54, 25.15, 23.,63, 22.39, 13.93.

IR (CDCl₃) cm⁻¹ 3590, 3510 (br), 1721, 1435, 1246, 1103, 885.

MS (CI—CH₄) m/e 353 (M+1), 335 (M+1—H₂O), 317 (M+1-2H₂O).

HRMS Calc for C₂₀H₃₃O₅ (M+1): 353.2327. Found 353.2286.

TLC (silica gel, ethyl acetate) R_f=0.45-0.53.

MP (from ethyl acetate/pentane) 137° C.

Minor macrolide (1,9-anhydro TXB₂):

¹H NMR (CDCl₃) delta 5.82-5.78 (1H, m), 5.72-5.60 (1H, m), 5.45-5.20 (3H, m), 5.0 (0.5H, br d, J=10 Hz), 4.9 (1H, br s), 4.45-4.35 (0.5H, m), 4.15-3.95 (2.5H, m), 2.4-1.2 (20 H, m), 0.86 (3H, br t, J—7 Hz).

¹³C NMR (CDCl₃) delta (major anomer) 174.28, 138.07, 132.08, 128.32, 125.94, 92.54, 72.24, 72.16, 69.70, 39.95, 36.76, 35.58, 33.55, 31.57, 29.49, 25.87, 25.44, 25.04, 22.47, 13.90.

IR (CDCl₃) cm⁻¹ 3592, 3440 (v br), 1733, 1450, 1149, 1088, 1035.

MS (CI—NH₃) m/e 370 (M+NH₄), 352 (M+), 335 (M—OH), 317 (M—OH—H₂O).

TLC (silica gel, ethyl acetate) R_f 0.27-0.35

In a 100 ml round bottom flask were placed 618 mg (1.75 mmol) of 1,15-anhydro TXB₂ (above), 1.35 gm (5.3 mmol, 3 equiv) of 2-chloro-1-methyl pyridinium iodide (Aldrich) and a magnetic stirring bar. A reflux condenser was attached and the apparatus was evacuated to about 0.05 Torr for 60 minutes. After venting with argon, 50 ml (0.035 M) of acetonitrile (freshly distilled from CaH₂) and 1.5 ml (11 mmol, 6 eq) of triethylamine were added. After refluxing for 90 minutes the solvent was removed on a rotary evaporator to give the crude enol ether.

¹H NMR (CDCl₃) delta 6.46 (1H, d, J=5.9 Hz), 6.04-5.94 (2H, m), 5.50 (1H, m), 5.44-5.29 (2H, m), 5.02 (1H, t, J=5.9 Hz), 4.13 (1H, dd, J=5.3, 11.2 Hz), 4.01 (1H, dd, J 3.6, 5.6 Hz), 2.43-2.30 (2H, m), 2.29-1.20 (16 H, m), 0.87 (3H, br t, J=7 Hz).

TLC (silica gel, 25% ethyl acetate/pentane) R_f=0.38.

The crude enol ether was immediately taken up in ether, washed twice with saturated aqueous NaHCO₃, filtered through Na₂SO₄, stripped to a volume of about 10 ml and transferred to a 100 ml round-bottom flask with ether (total volume ca 50 ml). Aqueous NaHCO₃ (4 ml of a 2% solution) was added and the solution was cooled to 0° C. 312 mg (1.75 mmol) of powdered N-bromosuccinimide was added to the well-stirred solution. After 15 minutes TLC indicated the complete consumption of starting material. The aqueous phase was then removed and the ethereal phase was washed three times with saturated aqueous NaHCO₃, dried over MgSO₄ and concentrated. The crude product was flash chromatographed on a 2.7 cm×15 cm silica gel column with a gradient of 20% to 30% ethyl acetate in petroleum ether to yield 496 mg (65%) of oily G as a 1:1 mixture of anomers.

$^1$H NMR (CDCl$_3$) delta 6.20-5.85 (2H, m), 5.5-5.2 (4H, m), 4.95 (0.5H, d, J=11 Hz), 4.40-4.05 (3.5H, m), 3.34 (0.5H, d, J=8 Hz), 3.27 (0.5H, d, J-12 Hz), 2.45-1.20 (17H), 0.86 (3H, br t, J=7 Hz).

$^{13}$C NMR (CDCl$_3$) delta 173.66, 134.31, 132.26, 131.86, 129.34, 129.23, 127.69, 127.99, 94.75, 89.21, 74.68, 70.51, 72.28, 70.00, 67.20, 57.25, 46.98, 41.63, 33.95, 33.82, 33.74, 31.30, 25.47, 25.41, 25.34, 25.12, 22.39, 20.19, 22.31, 13.95.

IR (CDCl$_3$) cm-1$^-$3510, 3600 (br), 1720, 1248, 1101, 1041.

MS (CI—CH$_4$) m/e 431 and 433 (M+1), 415 and 413 (M—OH), 397 and 395 (M—OH—H$_2$O), 333 (M—Br—H$_2$O).

HRMS Calc for C$_{20}$H$_{32}$$^{81}$BrO$_5$ (M+1): 433.1412. Found: 433.1384.

TLC (silica gel, 25% ethyl acetate/pentane) R$_f$=0.14-0.20.

EXAMPLE 5

10-Bromo 1, 15-Anydro Thromboxane A$_2$ (H$_1$)

To a stirred solution of 0.535 ml (4.5 mmol) freshly distilled trimethyl phosphite in 10 ml dry methylene chloride (0° C., nitrogen) was added azodicarboxylate. The ice bath was removed and the solution was stirred for an additional 5 minutes. The resulting pale yellow solution was added to a well-stirred solution of 650 mg (1.5 mmol) G in 20 ml dry methylene chloride at 0° C. under nitrogen. The ice bath was removed and the reaction mixture was stirred for 35 minutes at 25° C. The mixture was then concentrated to ca 4 ml and applied to a 2 cm×25 cm slurry-packed column of silica gel and rapidly eluted with 2% triethylamine/5% tetrahydrofuran in petroleum ether to give 108 mg (17.5%) of the pure bromooxetane H$_1$. The lower R$_f$byproducts were eluted from the column with ethyl acetate in petroleum ether to provide a recovery of 120 mg (18.5%) of starting material. The yield of H$_1$ based on consumed material is 21%.

$^1$H NMR (CDCl$_3$) delta 6.34 (1H, dd, J=16.1, 5.9 Hz), 6.15 (1H, dd, J=16.1, 8.6 Hz), 5.59 (1H, dd, J=3.9 3.3 Hz), 5.20-5.55 (2H, m), 5.17 (1H, m), 4.93 (1H, dd, J=5.9, 3.3 Hz), 4.83 (1H, dd, J=5.9, 3.9 Hz), 4.13 (1H, t, J=8.2 Hz), 2.39 (2H, ddd, J=12.5, 7.9, 2.6 Hz), 1.2-2.2 (15H, m), 0.88 (3H, t, J=6.3 Hz).

$^{13}$CNMR (CDCl$_3$) delta 172.89, 133.60, 132.81, 131.71, 127.11, 106.09, 85.68, 77.08, 71.51, 47.09, 45.50, 35.06, 32.92, 32.15, 26.80, 26.61, 26.34, 25.54, 23.24, 14.58.

IR (neat) cm$^{-1}$ 3010, 2955, 2932, 1727, 1242, 1074, 846.

MS (CI—CH$_4$) 413and 415 (M+1), 333 (M—Br).

HRMS Calcd for C$_{20}$H$_{29}$$^{81}$BrO$_4$: 414.1227. Found: 414.1209.

TLC (silica gel, 5% tetrahydrofuran/pentane) R$_f$=0.30.

EXAMPLE 6

1,15-Anhydro Thromboxane A$_2$ (H$_2$)

To a solution of 73 mg (0.176 mmol) H$_1$ in 5 ml dry pentane under argon was added 1.75 gm (ca 10 equiv SnH) polymer-bound tin hydride (8) and 3 mg recrystallized AIBN. The mixture was cooled under flowing tap water and stirred while irradiating with a 275 watt sunlamp. After appproximately 2 hours, TLC showed consumption of starting material and the polymer was removed by filtration. Solvent removal at reduced pressure gave H$_2$ (50 mg, 85%) as a crystalline solid. Recrystallization from pentane gave the X-ray sample (9) (MP=81°-82° C.). The product was not stable to silica gel chromatography and gave almost complete hydrolysis to 1,15-anhydro thromboxane B$_2$ on attempted analytical or preparative chromatography.

$^1$H NMR (C$_6$D$_6$) delta 6.29 (1H, dd, J=16.1, 6.3 Hz), 6.10 (1H, dd, J=16.1, 8.6 Hz), 5.60 (1H, dd, J=3.9, 3.3 Hz), 5.37-5.52 (2H, m), 5.36 (1H, m), 4.50 (1H, t, J=8.2 Hz), 4.48 (1H, dd, J=6.5, 3.9 Hz), 2.73 (1H, ddd, J=10.3, 6.5, 3.6 Hz), 1.2-2.4 (17H), 138 (1H, d, J=10.3 Hz), 0.95 (3H, t, J=6.7 Hz).

$^{12}$C NMR (C$_6$D$_6$) delta 172.71. 134.99, 132.20, 130.96, 128.17, 106.11, 82.19, 77.46, 71.53, 51.12, 42.28, 35.14, 32.92, 32.23, 26.79, 26.67, 26.29, 25.00, 23.21, 14.58.

IR (CH$_2$C$_2$) cm$^{-1}$ 3010, 2959, 2931, 1730, 1243, 1111, 1032.

MS (CI—CH$_4$) m/e 335 (M+1), 317 (M+1-H$_2$O).

HRMS Calcd for C$_{20}$H$_{31}$O$_4$ (M+1) 335.2222. Found: 335.2192.

TLC—Decomposition to 1,15-anhydro TXB$_2$.

This dehalogenation step can be omitted and one can proceed directly from the step of Example 5 to the step of Example 7 if a TXA$_2$ analog halogenated at the 10-position is desired as a final product.

EXAMPLE 7

Thromboxane A$_2$ Sodium Potassium (A)

A. Hydrolysis in Methanol/Water: To a vile containing 1 mg (0.003 mmol) H$_1$ in 0.050 ml (d$_4$-)methanol was immediately added 0.025 ml of a 0.12M solution of NaOH(D) in (D)H$_2$O under nitrogen. After stirring at 25° C. for 30 minutes, $^1$H NMR and biological assay showed the saponification to TXA$_2$ sodium to be complete. Such solutions were diluted and used for biological testing and could be stored for at least a week at −20° C. without significant loss in biological activity.

B. Aprotic Hydrolysis with Me$_3$SiOK: To 5 mg (0.015 mmol) H1 was added 0.10 ml (0.03 mmol) of 0.3M solution of Me$_3$SiOK (Petrarch) in anhydrous tetrahydrofuran (distilled from Ph$_2$CO/Na) or ether at 25° C. under argon. The solution slowly turned yellow and the reaction proceeded to completion over the course of 5 hours. The tetrahydrofuran or ether saponification solutions were used after dilution for biological testing. Saponification for NMR analysis was carried out in dry $d_8$-THF.

In a few instances, the methanol/water procedure has given substantial decomposition of the product TXA$_2$ sodium during the saponification. The Me$_3$SiOK/THF hydrolysis procedure on the other hand is highly reproducible and is thus preferred.

$^1$H NMR , delta (potassium salt) 5.87 (2H, br t, J=9 Hz, H13, H14), 5.73 (1H, t, J=4 Hz, H11), 5.45-5.70 (2H, m, H5, H6), 4.72 (1H, dd, J=4, 6 Hz, H9), 4.53 (1H, br t, J=6 Hz, H12), 4.18 (1H, br q, J=6 Hz, H15), 3.22 (1H, m, H10a), 1.4-2.5 (18H, m), 1.05 (3H, br t, H20). All peaks were broadened (w/2 ca 2 hz) possibly due to slow exchange of the salt aggregates.

Further physical characterization was not possible due to the lability of the TXA$_2$ salts.

If the dehalogenation step of Example 6 is omitted and 10-bromo-1,15-anhydro Thromboxane A$_2$ or 10-chloro-1,15-anhydro Thromboxane A$_2$ is hydrolyzed directly the resulting product will be a 10-chloro or 10-bromo analog of TXA$_2$.

EXAMPLE 8

Although macrolide H$_2$ (X=H) did not show the biological properties of TXA$_2$, it was saponified in NaOD/D$_2$O/CD$_3$OD (30 minutes, 22° C.) as evidenced by $^1$H NMR which showed opening of the 1,15-macrolactone with retention of the bicyclic oxetane nucleus to yield the synthetic A (TXA$_2$S) as its sodium salt which did exhibit biological properties. TXA$_2$S was also prepared by saponification of H$_2$ (X=H) with Me$_3$.SiOK (10) in tetrahydrofuran and isolated as an amorphous solid by solvent evaporaton. While TXA$_2$S underwent rapid decomposition in neutral or acidic solutions, it is relatively stable in the basic saponification solutions described and could be stored for up to a week at $-20°$ C. without significant loss in activity.

TXA$_2$S at concentrations of 16-100 nanograms/ml caused a concentration-dependent aggregation of human platelet rich plasma (PRP). Irreversible aggregation occurred with 50-100 nanograms TXA$_2$S/ml for all cases examined. TXA$_2$S was found to be approximately 10 times more potent than the prostaglandin endoperoxide PGH$_2$ at inducing aggregation of human PRP. These comparative potencies concur with published data. (12,13) TXA$_2$S (10 ug/ml) decayed in human plasma by first order kinetics with a half-life of 3.9 minutes at 37° C., consistent with values of 3 minutes (14) and 5-6 minutes (15) determined by indirect methods with biologically generated material. The aggregatory effects of TXA$_2$S were confined to platelets. At 2 ug/ml it did not aggregate human neutrophils nor did it stimulate formation of leukotriene B$_4$.

A selective thromboxane synthetase inhibitor with no accompanying receptor level antagonist properties (9,11-iminoepoxy-prosta-5,13-dienoic acid (U-54701)) at 5-15 ug/ml, had no effect on platelet aggregation induced by TXA$_2$S. In contrast, a related compound with receptor level antonist properties (9,11-diazoprosta-5,13-dienoic acid (U-51605)) at 1-3 ug/ml inhibited TXA$_2$-induced aggregation in a concentration-dependent manner. (16)

Hydrolysis of TXA$_2$S in 0.1 M phosphate buffer, pH 7.4, eliminated its biological activity and produced a substance that was immunologically indistinguishable from synthetic TXB$_2$. Radioimmunoassay determinations of hydrolyzed TXA$_2$ yielded values of 84±21, 60±16, 39±11, and 25±8 picograms TXB$_2$ (mean±S.D at 95% confidence, n=3) which correspond with predicted values of 125, 62, 31, and 15 picograms, respectively. The half-life of TXA$_2$S at 37° C. in Krebs solution measured by bioassay on vascular tissue was 30 seconds which compares very closely with previously reported half-lives for biologically generated material. (1, 12)

The rabbit aorta contracting substance detected by Piper and Vane (17) in the effluent of perfused guinea pig lung during anaphylaxis was shown to be a mixture of TXA$_2$ and prostaglandin endoperoxides. Similarly TXA$_2$ generated by platelets or a partially purified platelet enzyme has potent vascular contracting activity. Thus both natural and synthetic TXA$_2$ contracted all vascular tissue tested including Krebs superfused (18) rabbit aorta, pulmonary, mesenteric, celiac arteries and bovine coronary arteries. On most tissues 2-3 ng of TXA$_2$S was the threshold dose for contraction, generating more than 2 g of tension with rabbit aorta and 4 g of tension with bovine coronary arteries. The potency of TXA$_2$S compared well with the activity of biologically produced TXA$_2$ which was calculated from the amount of PGH$_2$ originally in the incubation (assuming 100% conversion). Rabbit mesenteric and celiac arteries respond to PGH$_2$ with a small, short-lived contraction, followed by larger, longer lasting relaxation (19) whereas TXA$_2$S and biologically generated TXA$_2$ gave only constriction.

Although these experiments do not rule out the formal possibility that A is not TXA$_2$ itself but is converted in vivo to a different material which is the endogenous TXA$_2$, the qualitative and quantitative activity and the half-life of TXA$_2$S provide strong evidence that the Samuelsson oxetane structure (A) for TXA$_2$ is correct.

References

1. Hamberg, M., Svensson, J., and Samuelsson, B. Proc. Natl. Acad. Sci. U.S.A., 72, 2994-2998 (1975).
2. Bhagwat, S. S., Hamann, P. R. and Still, W. C. Tetrahedron Lett., in press. Previously reported hetero-substituted derivatives: Ito, H., Eby, R., Kramer, S., and Schuerch, C. Carbohydr. Res., 193-202 (1980); Varma, A. J., and Schuerch, C. J. Org. Chem., 46, 799-803 (1981); Kong F., and Schuerch, C. Carbohydr. Res., 112, 141-147 (1983); Fried J., Hallinan, E. A., and Szedo, M. J. J. Am. Chem. Soc., 106, 3871-3872 (1984).
3. Granstorm, E., Diczfalusy, U., Hamberg, M., Hansson, G., Malmsten, C., and Smuelsson, B., "Prostaglandins and the Cardiovascular System," John A. Oates, Ed., Raven press, New York, (1982).
4. Review: Mitsunobu, O. Synthesis. 1-28 (1981).
5. Corey, E. J., Nicolaou, K. C., Melvin, L. S. J. Am. Chem. Soc., 97 653-654 (1975); Narasaka, K., Maruyama, K., and Mukaiyama T. Chemistry Lett., 885-888 (1978); Bundy, G. L., Peterson, D. C., Cornette, J. C., Miller, W. L., Spilman, C. H., and Wilks, J. W. J. Med. Chem., 26, 1089-1099 (1983).
6. Corey, E. J., and Nicolaou, K. C. J. Am. Chem. Soc., 96, 5614-5616 (1974); Corey, E. J., and Clark, D. A. Tetrahedron Lett., 2875-2878 (1979).
7. Mukaiyama, T., Usui, M., and Shimada, E. Chem. Lett., 1045-1048 (1975).
8. Weinshenker, N. M., Crosby, G. A., and Wong, J. Y. J. Org. Chem., 40, 1966-1971 (1975).
9. Chiang, M., to be reported in detail elsewhere.
10. Laganis, E. D., and Chenard, B. L. Tetrahedron Lett., 25, 5831-5834 (1984).
11. Bhagwat, S. S., Hamann, P. R., Still, W. C., Bunting, S., and Fitzpatrick, F. A. Nature, in press.
12. Needleman, P., Moncada, S., Bunting, S., Vane, J., Hamberg, M., and Samuelsson, B. Nature, 261, 558-560 (1976).
13. Needleman, P., Minkes, M., and Raz, A. Science, 193, 163-165 (1976).
14. Folco, G., Granstrom, E. Kindahl, H. FEBS Lett., 82, 321-324 (1977).
15. Smith, J. B., Ingerman, C., and Silver, M. J. Clin. Invest., 58, 1119-1122 (1976).
16. Fitzpatrick, F., Gorman, R., Bundy, G., Honohan, T. McGuire, J., and Sun, F. Biochim. Biophys. Acta, 573, 238-244 (1979).
17. Piper, P. J., and Vane, J. R. Nature 223, 29-35 (1969).
18. Vane, J. R., Brit. J. Pharmacol., 12, 344-349 (1957).
19. Bunting, S., Moncada, S., and Vane, J. R. Brit. J. Pharmacol., 57, 462 (1976).

What is claimed is:
1. A compound having the structure:
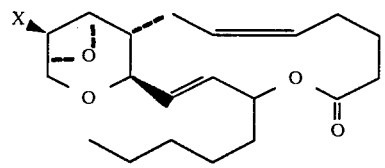
wherein X may be hydrogen, bromine, chlorine, fluorine or iodine.
2. The compound of claim 1, wherein X is bromine.
* * * * *